United States Patent [19]

Swerczek

[11] Patent Number: 4,483,851

[45] Date of Patent: Nov. 20, 1984

[54] TREATMENT FOR CONTAGIOUS EQUINE METRITIS

[75] Inventor: Thomas W. Swerczek, Lexington, Ky.

[73] Assignee: The University of Kentucky Research Foundation, Lexington, Ky.

[21] Appl. No.: 409,180

[22] Filed: Aug. 18, 1982

[51] Int. Cl.³ ............................................. A61K 31/70
[52] U.S. Cl. ..................................................... 424/180
[58] Field of Search ........................................ 424/180

[56] References Cited

U.S. PATENT DOCUMENTS

| 327,230 | 9/1885 | Carnrick. | |
| 2,118,566 | 5/1938 | Miles | 167/96 |
| 2,139,139 | 12/1938 | Tompkins | 167/55 |
| 2,354,319 | 7/1944 | Inman | 167/96 |
| 2,826,533 | 3/1958 | Fowell | 167/74 |
| 2,895,882 | 7/1959 | Thorne et al. | 195/96 |
| 4,083,958 | 4/1978 | Bryans | 424/89 |

OTHER PUBLICATIONS

Swaney et al., American Journal of Veterinary Research, vol. 41, Jan., 1980, pp. 127-132.
John P. Hughes, Theriogenology, Dec. 8, 1978.
Henry J. Dabernat et al., Antimicrobial Agents and Chemotherapy, Dec., 1980, pp. 841-843.
S. P. Sahu et al., American Journal of Veterinary Research, vol. 1, pp. 1379-1382.

Primary Examiner—Johnnie R. Brown
Assistant Examiner—Elli Peselev
Attorney, Agent, or Firm—Lowe, King, Price & Becker

[57] ABSTRACT

A composition is provided for the treatment of contagious equine metritis, a contagious veneral disease of horses, which composition comprises an aqueous solution of dextrose, a buffering mixture to provide a pH of about 3.0 to 4.5, and a carrier, the composition being applied topically to external genitalia of horses.

14 Claims, No Drawings

TREATMENT FOR CONTAGIOUS EQUINE METRITIS

FIELD OF THE INVENTION

This invention relates to methods for the treatment of contagious equine metritis and more particularly to novel compositions useful for the treatment of contagious equine metritis by topical application.

BACKGROUND OF THE INVENTION

Contagious equine metritis (CEM) is a highly contagious venereal disease of horses caused by a fastidious, gram-negative cocobacillus. The disease is characterized by a copious water-to-mucopurulent vaginal discharge 2-10 days after breeding by an infected stallion. Shortened estrous cycle links are common and may be the only indication of endometritis in some instances. Carriers of the disease are difficult to detect but outbreaks of the disease have been reported in England, Ireland, France, Australia and in the United States. As reported by Swaney et al, American Journal of Veterinary Research, Vol. 41, January, 1980, pps. 127-132, the causative agent of contagious equine metritis has been identified as *Haemophilus equigenitalis,* which has ultrastructural characteristics of gram-negative bacteria. The Haemophilus equigenitalis is microaerophilic and unreactive biochemically. It does not depend on hemin (X factor) or nicotinamide adenine dinucleotide (V factor) for growth although hemin stimulates growth.

Various proposals have been made for treatment of the disease with modest success. Thus, in the article by Swaney et al, there is disclosure that streptomycin can be used against the bacteria. Further, in the article by John P. Hughes in Theriogenology, published Dec. 8, 1978, it is reported that a wide range of antibiotic and antimicrobial agents have been used either topically, parenterally or in combination at varying dose rates and over different periods of time. Included are suggestions for the use of intrauterine antiseptic solutions, washing with surgical soap, rinsing and applying 0.3% nitrofurazone ointments and the like but the most common treatment is indicated as being the intrauterine infusion of benzyl penicillin or ampicillin for a period of 3 to 5 days.

In the article by Henry J. Dabernat et al in Antimicrobial Agents and Chemotherapy, December 1980, pps. 841-843, a review of this disease is disclosed with the statement that the most active drugs are ampicillin, gentamicin, and tetracycline, although a number of other materials were tested with negative results. In an article by S. P. Sahu et al appearing in American Journal of Veterinary Research, Vol. 41, September 1980, pps. 1379-1382, there is described a review of the disease and the use of a citrate-phosphate buffer for a sugar compound to isolate and identify the bacteria but not as a method of treatment.

It is evident from this literature that there remains a need in the art for a simple, effective method for the treatment of animals infected with this disease and the present invention provides compositions and methods which are effective for this purpose.

SUMMARY OF THE INVENTION

It is accordingly one object of the present invention to provide a composition which is effective for the treatment of contagious equine metritis.

A further object of the invention is to provide a method for the treatment of contagious equine metritis.

A still further object of the present invention is to provide a topical composition and methods for its use in the treatment of contagious equine metritis in horses.

Other objects and advantages of the present invention will become apparent to those skilled in the art as the description thereof proceeds.

In satisfaction of the foregoing objects and advantages there is provided by this invention a composition for the treatment of contagious equine metritis which comprises an aqueous solution of dextrose or a dextrose metabolite, a buffering mixture of weak organic acids and alkali metal salts of weak organic acids, and a carrier, the composition being characterized as a viscous solution having a pH of about 3.0 to 4.5. Also provided by the present invention is a method for application of this composition to horses for the treatment of contagious equine metritis which comprises topically applying an effective amount of the composition to the external genitalia of stallions and mares.

Description of Preferred Embodiments

As pointed out above, the present invention is concerned with novel compositions and a method for the treatment of contagious equine metritis, which is a relatively newly recognized venereal disease in horses, the causative organism being *Haemophilus equigenitalis.* The disease is wide-spread throughout the world and has also been found to be present in horses in the United States. While there are treatments available for the disease as discussed above, primarily by antibiotics, these treatments cause irritation to the mucous membranes. Super bacterial infections, primarily pseudomonas infections, are commonly the end results of the prior art treatment.

The present invention provides a novel composition of matter which can be applied topically without the disadvantages and side effects of the prior art treatments. The composition of the present invention in its broadest embodiment comprises an aqueous solution of dextrose or a dextrose metabolite, a buffering mixture of weak organic acids and/or alkali metal salts of weak organic acids, and a carrier, the solution being characterized as a relatively viscous solution having a pH ranging from about 3.0 to 4.5.

In several trials the composition was found to be 100% effective in curing horses of the disease if used on three successive days. By comparison antibiotics currently used have to be applied for at least 5 days and are not 100% effective.

The most preferred composition may be characterized as containing the following formulation in water in a concentration of about 40-60 weight percent:

| Ingredient | Parts by Weight |
| --- | --- |
| Dextrose | 200-300 |
| Buffering Mixture | 40-110 |
| Carrier | 80-110 |

The dextrose component of the composition is dextrose or a dextrose metabolite which is effective to inhibit the contagious equine metritis organism. The dextrose component is an important ingredient as it appears that the dextrose or a metabolite of dextrose inhibits the contagious equine metritis organism. Accordingly, dextrose or equivalent material may be used in the composition.

The buffering mixture is also an important ingredient of the composition. A sufficient amount of buffer should be present to provide a resulting solution having a pH of about 3.0 to 4.5, most preferably in the range of 3.2. Any buffer or mixture of buffers can be used for this purpose although mixtures of weak organic acids and alkali metal salts of organic acids are especially preferred. The amount of buffering agent present is also important since the total solution should contain about 8 to 15 weight percent of buffering agents for a suitable composition.

The preferred buffering agents are polycarboxylic acids, phosphates, and the like which will provide the required pH range. The most preferred buffers however comprise a mixture of hydroxy polycarboxylic acids having about 3 to 8 carbon atoms and their alkali metal salts, or mixtures thereof. Preferred organic acids include citric acid, malic acid, tartronic acid, tartaric acid, and mixtures thereof as well as the sodium and potassium salts of the acid. A highly preferred buffering system comprises a mixture of citric acid and sodium citrate.

It is also preferred that the resulting solution be a viscous solution to inhibit drainage from the infected organs after topical application. Thus, a carrier vehicle is included in the composition to increase the viscosity of the solution. Suitable carries include polyalkylene glycols, methyl cellulose and the like. The preferred carrier vehicle is a lower polyalkylene glycol such as glycerine.

The carrier also provides the proper consistency to the composition so that the composition can be used as a lubricant in the treatment of animals such as horses. Thus, the composition will provide both lubricating properties and effectively treat contagious equine metritis on application to horses.

A preferred formulation is a 40–60 weight percent aqueous composition of the following materials:

| Ingredient | Amount-Parts |
|---|---|
| Dextrose | 200–300 |
| Hydroxy carboxylic acid | 25–75 |
| Alkali metal salt of Hydroxy carboxylic acid | 40–110 |
| Carrier | 80–110 |

The most preferred composition for use in the present invention is as follows:

| Ingredient | Amount |
|---|---|
| Dextrose | 250 grams |
| Citric Acid | 50 grams |
| Sodium Citrate | 25 grams |
| Glycerine | 100 ccs. |
| Water | 400 ccs. |

The resulting composition is in an aqueous solution with sufficient consistency to drain slowly. In use the composition is applied topically directly to the external genitalia of stallions and mares and preferably is used one time each day for at least two successive days. An effective amount is simply a thorough application of the viscous solution to the external genitalia manually. It has been found that this method will provide 100% effectiveness in curing horses of the contagious equine metritis organism-caused disease.

The following example is to illustrate the invention but the invention is not to be considered as limited thereto. In the Example and throughout the specification, parts are by weight unless otherwise indicated.

EXAMPLE

The following composition was prepared:

| Ingredient | Parts by Weight |
|---|---|
| Dextrose | 250 grams |
| Citric Acid | 50 grams |
| Sodium Citrate | 25 grams |
| Glycerine | 100 ccs. |
| Water | 400 ccs. |

The resulting composition was a viscous solution having a pH of 3.20.

To show the effectiveness of the compound twenty horses were selected for testing. Each of the twenty horses was treated with a single treatment of the solution by manually applying topically directly to the external genitalia of the horses. From this test, 17 of the horses were found to be cured by the single treatment. The three horses which were not cured with the single treatment were then treated again with two successive treatments which were found to successfully cure the disease. Accordingly, in the field it is recommended that the disease be treated one time per day with application of the composition on at least two successive days.

The advantages in use of the composition of the present invention in the treatment of contagious equine metritis over current therapy and the antibiotics used in the prior art are several. Thus, the horses do not have to be scrubbed prior to treatment, the treatment does not irritate the mucous membranes and the skin, and the treatment does not cause super bacterial infections. Moreover, the treatment is effective for pseudomonas as well as for the contagious equine metritis organism. Moreover, only about two to three treatments are necessary and mares can be treated successfully without removing the clitoral sinuses.

The invention has been described herein with reference to certain preferred embodiments. However, as obvious variations thereon will become apparent to those skilled in the art, the invention is not to be considered as limited thereto.

What is claimed is:

1. A composition for the treatment of contagious equine metritis which comprises an antimicrobial-effective amount of dextrose in an aqueous based mixture including a buffer present in sufficient amounts to provide a pH in the range of about 3.0 to 4.5, and a carrier, said composition comprising the following: 200 to 300 parts by weight of dextrose, 40 to 110 parts by weight of buffer, and 80 to 110 parts by weight of a carrier, contained in about a 40 to 60 weight percent concentration in water.

2. A composition according to claim 1 which comprises about 200–300 parts of dextrose, about 25–75 parts of a hydroxy carboxylic acid, about 40–110 parts of an alkali metal salt of a hydroxy carboxylic acid and about 80–110 parts of a carrier.

3. A composition according to claim 2 wherein the hydroxy polycarboxylic acid component is selected from the group consisting of citric acid, tartronic acid, malic acid, tartaric acid, and mixtures thereof.

4. A composition according to claim 2 wherein the alkali metal salt of the hydroxy polycarboxylic acid is selected from the group consisting of sodium and potassium salts of citric acid, tartronic acid, malic acid, tartaric acid, and mixtures thereof.

5. A composition according to claim 2 wherein the carrier is a polyalkylene glycol.

6. A composition according to claim 1 which comprises 250 parts dextrose, 50 parts citric acid, 25 parts sodium citrate, 100 ccs. glycerine and 400 ccs. water, said composition being in the form of a viscous solution hving a pH in the range of 3.2.

7. A method for the treatment of contagious equine metritis in horses which comprises topical application to the external genitalia of horses of an antimicrobial-effective amount of dextrose in an aqueous based mixture including a buffer present in sufficient amounts to provide a pH in the range of about 3.0 to 4.5, and a carrier.

8. A method according to claim 7 wherein the components of the composition are contained in about a 40-60 weight percent concentration in water and are present in the following amounts by weight:

| Ingredient | Parts by Weight |
| --- | --- |
| Dextrose | 200-300 |
| Buffer | 40-110 |
| Carrier | 80-110. |

9. A method according to claim 8 wherein the composition comprises about 200-300 parts of dextrose, about 25-75 parts of a hydroxy carboxylic acid, about 40-110 parts of an alkali metal salt of a hydroxy carboxylic acid and about 80-110 parts of a carrier.

10. A method according to claim 9 wherein the hydroxy polycarboxylic acid component is selected from the group consisting of citric acid, tartronic acid, malic acid, tartaric acid, and mixtures thereof.

11. A method according to claim 9 wherein the alkali metal salt of the hydroxy polycarboxylic acid is selected from the group consisting of sodium and potassium salts of citric acid, tartronic acid, malic acid, tartaric acid, and mixtures thereof.

12. A method according to claim 9 wherein the carrier is a polyalkylene glycol.

13. A method according to claim 7 wherein the composition comprises 250 parts dextrose, 50 parts citric acid, 25 parts sodium citrate, 100 ccs. glycerine and 400 ccs. water, said composition being in the form of a viscous solution having a pH in the range of 3.2.

14. A method according to claim 7 wherein the composition is topically applied to the external genitalia of the horses one time per day for at least two successive days.

* * * * *